(12) United States Patent
Kitagawa et al.

(10) Patent No.: US 6,919,956 B2
(45) Date of Patent: Jul. 19, 2005

(54) METHOD OF AUTOMATICALLY REPAIRING CRACKS AND APPARATUS FOR USE IN SUCH METHOD

(75) Inventors: Tomoaki Kitagawa, Takasago (JP); Ken Fujita, Takasago (JP); Toshihiko Tsunatani, Takasago (JP); Masahiko Mega, Takasago (JP); Yasushi Takeuchi, Takasago (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 253 days.

(21) Appl. No.: 10/245,342

(22) Filed: Sep. 18, 2002

(65) Prior Publication Data

US 2003/0095250 A1 May 22, 2003

(30) Foreign Application Priority Data

Nov. 19, 2001 (JP) .................................... 2001-353065

(51) Int. Cl.[7] ............................................ G01N 21/00
(52) U.S. Cl. .................. 356/237.1; 356/237.2
(58) Field of Search .......................... 356/237.1–237.2; 29/889.1, 889.7, 402.13, 402.16, 402.18; 250/458.1, 459.1, 461.1; 382/141

(56) References Cited

U.S. PATENT DOCUMENTS 4,803,639 A 2/1989 Steele et al.
5,961,859 A * 10/1999 Chou et al. ............. 219/121.63
6,195,891 B1 * 3/2001 Chen et al. ................. 29/889.1
2002/0128790 A1 * 9/2002 Woodmansee ............... 702/81

FOREIGN PATENT DOCUMENTS

| DE | 1106037 | 5/1961 |
| DE | 8909840 | 12/1990 |
| JP | 6-344144 | 12/1994 |
| JP | 9-145340 | 6/1997 |

* cited by examiner

Primary Examiner—Michael P. Stafira
(74) Attorney, Agent, or Firm—Wenderoth, Lind & Ponack, L.L.P.

(57) ABSTRACT

A method and apparatus automatically repairs cracks produced in a member to be repaired. A wide field image is obtained by photographing the whole surface of a blade 31 or the like in a wide field view by a remote camera 11 and the position of cracks on the surface of the blade is obtained as a rough position information of the cracks by processing the image of wide field view. Then the cracks are photographed in a narrow field view at the predetermined spacing along the cracks based on the rough position information by a light section method. The narrow field images are processed to obtain the position, width, and depth of the crack at each predetermined spacing, which compose crack data at the series of points, and the cracks are repaired based on the crack data at the series of points.

8 Claims, 6 Drawing Sheets

METHOD OF AUTOMATICALLY REPAIRING CRACKS AND APPARATUS FOR USE IN SUCH METHOD

BACKGROUND OF THE INVENTION

1. Field of the Invention

The present invention relates to a method of repairing automatically the cracks in a member to be repaired and an apparatus for use in such a method, specifically a method of repairing automatically the cracks produced in a blade, etc. of a rotary machine and an apparatus for use in such a method.

2. Description of the Related Art

Generally, cracks tend to occur in a blade, etc. of a rotary machine (for example in a turbine blade) owing to the severe environment of operation. Therefore, it is required in the operation of a turbine, etc. to periodically check if a crack is produced or not. To be concrete, the blades are checked after the operation of the turbine, and if a crack is found, the crack is repaired.

Recently, apparatuses for automatic welding have been developed. Welding can be carried out automatically by the use of such an automatic welding apparatus. However, in the case of repairing cracks, the states of cracks are diverse and it is difficult to repair the cracks by using an automatic welding apparatus. To be more specific, when repairing cracks by welding, the welding must be performed according to the direction, position, depth, etc. of the cracks, so the repair of cracks by an automatic welding apparatus has been difficult.

Therefore, the repair of the crack produced in the blade, etc. has been carried out by handwork, in which the position, width, depth, etc. of the crack are recognized by hand, the aperture of the crack is ground, then the ground portion is welded by hand welding.

When the crack has been repaired, as has been described above, by handwork, recognizing by hand the position, width, depth, etc., grinding the aperture of the crack, then welding the ground part by hand welding, a proficiency has been required in the repair, and in addition, the grinding and welding should have been carried out according to the result of careful examination of the crack. Therefore, when considering the diversity of the states of cracks, the number of processes inevitably increases for repairing the crack produced in a member to be repaired such as a blade, etc.

Further, since skill is required for repairing cracks as mentioned above, the result of repair is dependent on the skill of a welder, so there occurs the problem that stable quality of the repaired part is not assured.

To overcome the disadvantage mentioned above, an invention was disclosed in Japanese Patent Application Publication No. 9-145340, for example, for reducing the man-hours required to detect and measure cracks at inspection or for automatization of these steps concerning gas turbine blades.

According to the disclosure, the apparatus is composed of, as shown in FIG. 7(A), a detector (camera) 121 to detect cracks, a driver 122 to drive the detector, a position controller 123 to control the position of the driver, an image processing apparatus 124 to process the image information of the surface of a stator vane input from the detector, a calculation operation unit 125 to determine the degree of damage such as the maximum crack length, sum of crack lengths, etc. by measuring crack lengths from the processed image, and a memory 126 to store the data of the shapes of stator vanes. With the apparatus, the detected image of a crack is divided properly, and the coordinates of each point of division $c_1, c_2, c_3, \ldots$ are projected on real shape model to determine the real crack length, as shown in FIG. 7(B).

However, in the art mentioned above, the measurement in the case of a branched crack is not taken into consideration. Further, when projected in a wide field of vision, the depth of the crack can not be determined, and when projected in a narrow field of vision, the path of the crack can not be judged. As a result, the accuracy of determination of cracks decreases.

SUMMARY OF THE INVENTION

The objective of the present invention is to provide a method of automatically repairing cracks and an apparatus for use in such a method, by which a crack produced in a member to be repaired can be automatically repaired with good accuracy.

According to the present invention, a method of automatically repairing cracks has a first step of obtaining rough position information on the cracks, which is information of the presence and absence of cracks and the position thereof, by processing a wide field image obtained by taking a picture of the member to be repaired in a wide field of view. A second step obtains crack data at a series of points along the cracks, which is information of the position, width, and depth of the cracks at each point having a spacing predetermined along the cracks and is determined by processing a narrow field image of the cracks photographed at each point spaced by the predetermined spacing based on the rough position information.

After the crack data at the series of points is obtained, the cracks are repaired according to the crack data at the series of points. For example, first the cracks are ground according to the crack data at the series of points, then the cracks are welded according to the crack data at the series of points. A light section method is used to obtain the crack data at the series of points. The predetermined spacing is a distance between adjacent points of photography and the distance is determined in a range so that a line segment connecting said adjacent points of photography can be assumed as a straight-line segment.

As the repair of the cracks is done by obtaining the crack data at the series of points by image processing thereof and then repairing the cracks according to the crack data at the series of points, automatic repair of cracks is possible.

Further, according to the present invention, an automatic repairing apparatus used in repairing the cracks produced in the member to be repaired is provided with a first photographing means to take the picture of the member to be repaired in a wide field view in order to obtain the wide field image thereof. An image processing means obtains rough position information of the cracks, which is information of the presence and absence of cracks and the position thereof in the member to be repaired, by processing the wide field image. A second photographing means obtains a narrow field image of the cracks by photographing the cracks at each point having a spacing predetermined based on the rough position information in a narrow field view, the processing means processes the narrow field image to obtain the crack data at the series of points, which is the information of the position, width, and depth of the cracks at each point spaced by a predetermined distance, by processing the narrow field image.

After the crack data at the series of points is obtained, the cracks are ground according to the crack data at the series of points, and then the cracks are welded according to the crack data at the series of points. A light section method is used to obtain the crack data at the series of points.

A light section method in the field of welding is well known. As disclosed in Japanese Patent Application Publication No.6-344144, and in FIG. 6 herein, reference numeral 101 is a welding torch, 102 is a CCD camera, 103 is a laser slit light source slanted by determined angles with regard to the CCD camera 102, 104 is a laser slit light emitted from the light source 103, 105 is a groove face, 106 is an image processing apparatus, 107 is a monitor, 108 is a welding electrode, 110 is a welding wire, 112 are welded beads, and 114 is a interference filter. The laser slit light 104, which is a laser light flux emitting through a slit, irradiates the groove face 105 at a right angle to the weld line. The light section image obtained in accordance with the groove shape is received by the camera via the interference filter, which passes light of the same wavelength as the laser light. The shape of the groove is determined by processing the image received by the CCD camera with the image processing apparatus 106. For example, the laser split light of wavelengths of 600~800 nm is emitted intermittently at an interval of a short time, and image processing is performed to take out the image containing only the laser slit light by detracting the image not containing the laser slit light from that containing the laser slit light or by taking an exclusive OR of both images.

DETAILED DESCRIPTION OF THE PREFERRED EMBODIMENT

A preferred embodiment of the present invention will now be detailed with reference to the accompanying drawings. It is intended, however, that unless particularly specified, dimensions, materials, relative positions and so forth of the constituent parts in the embodiments shall be interpreted as illustrative only not as limitative of the scope of the present invention.

The present invention will now be explained hereunder by taking as an example the case of repairing the crack produced in a turbine blade. However, the present invention can be applied similarly to the case of repairing a member (member to be repaired) other than a turbine blade.

Figure 1:
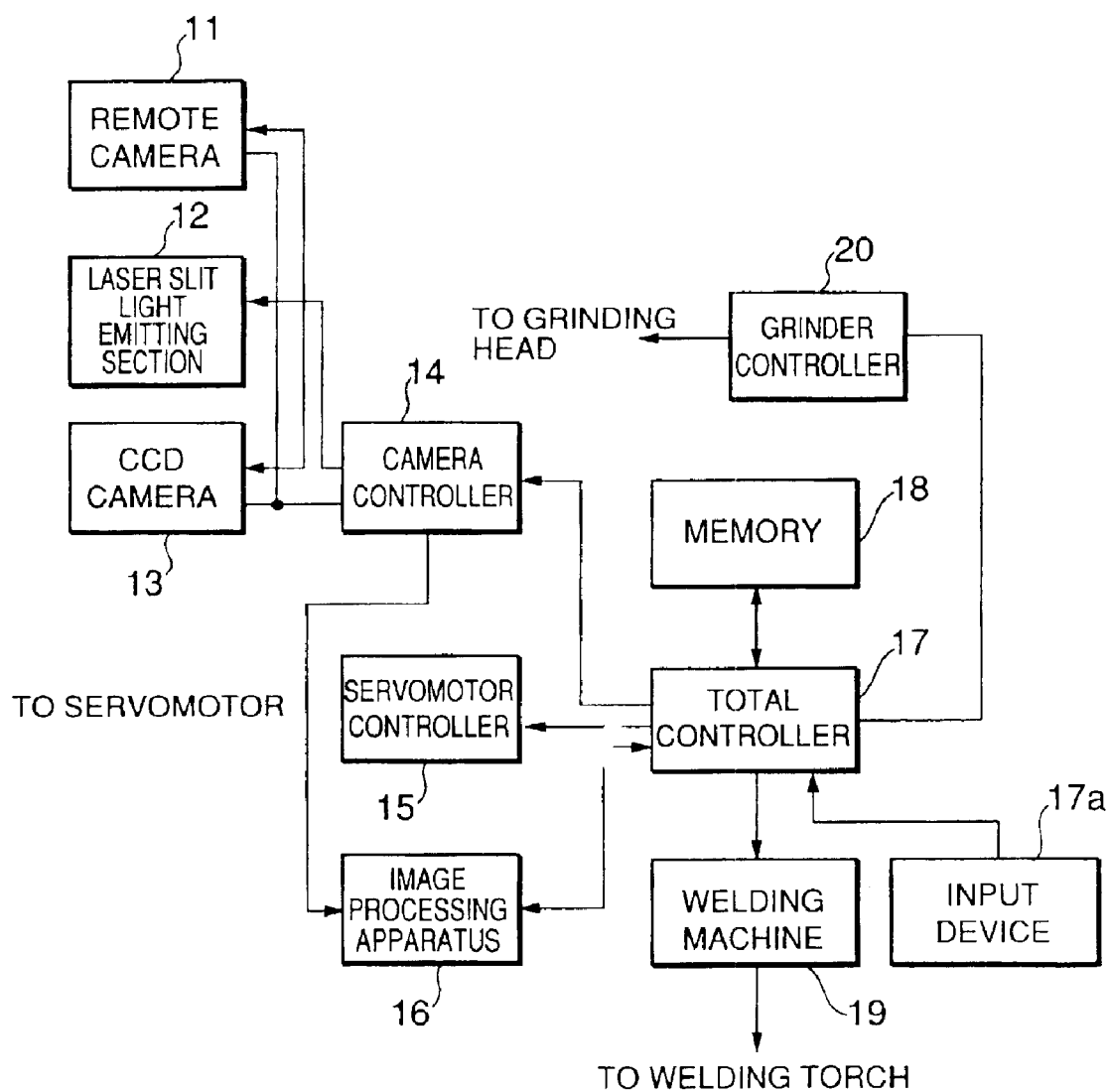
FIG. 1 is a block diagram showing an example of a control system of an apparatus for automatically repairing cracks according to the present invention.

Referring to FIG. 1, the automatic crack repairing apparatus is provided with a remote camera 11, a laser slit light emitting section (laser slit sensor) 12, a CCD camera 13, a camera controller 14, a servomotor controller 15, an image processing apparatus 16, a total controller 17, an input device 17a, a memory 18, a welding machine 19, and a grinder controller 20. When grinding is carried out, the total controller 17 controls a grinding head (for example, a pencil type grinding head, not shown in the drawing) via the grinder controller 20. On the other hand, when welding is performed, the total controller 17 controls the welding head (not shown in FIG. 1) via the welding machine 19.

Figure 2:
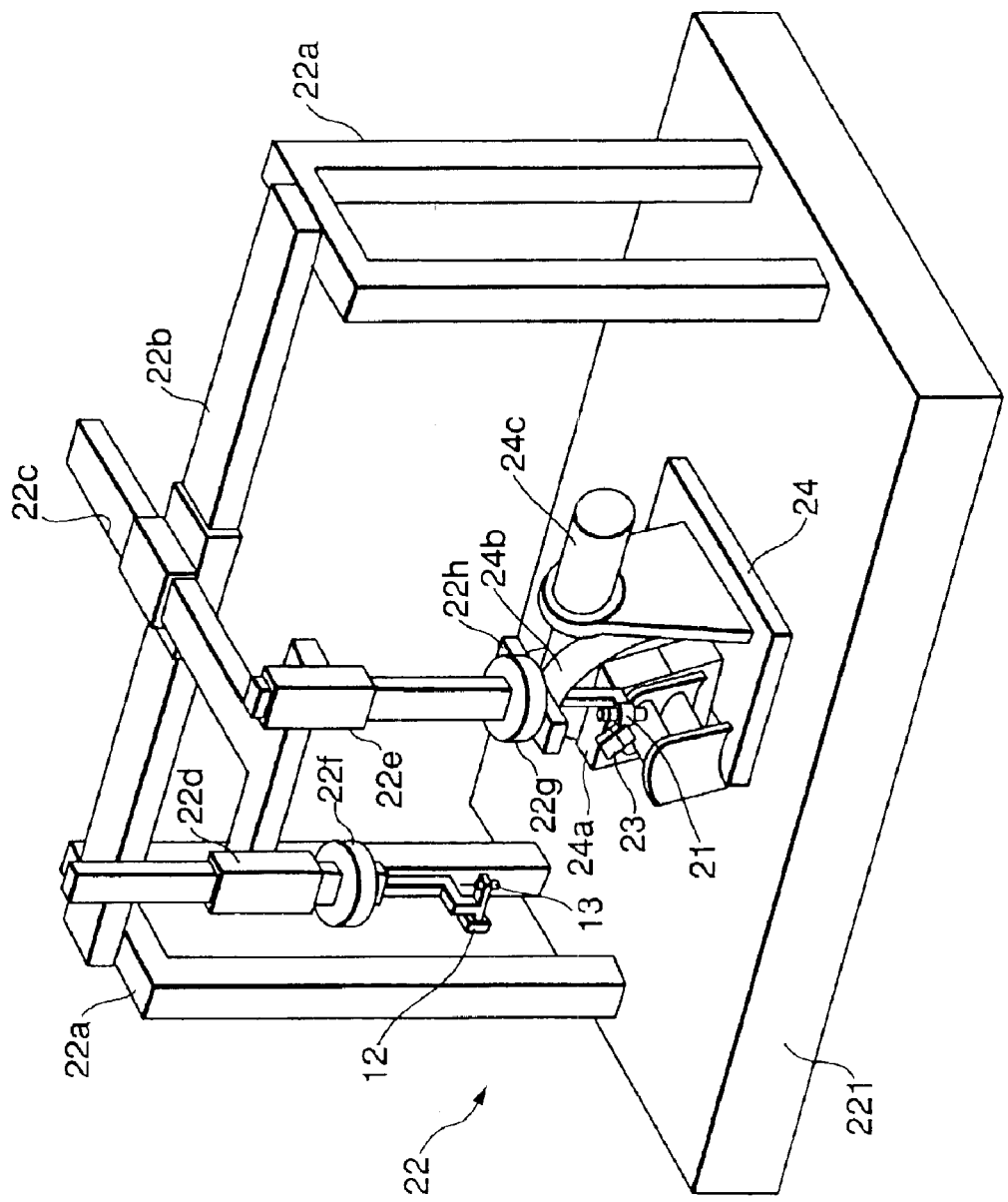
FIG. 2 is an example of a driving mechanism of the apparatus for automatically repairing cracks according to the present invention.

Referring to FIG. 2, welding torch 21 is controlled, as described later, by the welding machine 19 via the total controller 17. The welding torch 21 is mounted to a transfer apparatus 22 and manipulated by the total controller 17 to move in three directions of X, Y, and Z, including a weaving motion via the servomotor controller 15.

A wire supplier 23 is provided near the welding torch 21. When welding is carried out, welding wire is supplied to the top end part of the welding torch 21 by the wire supplier 23. The laser slit light emitting section 12 emits laser slit light (laser light passing through a slit) onto the crack in the blade so that the light crosses the aperture of the crack. The CCD camera 13 receives the laser slit light in the direction inclined by a determined angle against the radiating direction to grasp the section of the aperture of the crack by the light section method, and the received light is sent to the camera controller 14. The laser slit light emitting section 12 is attached to the transfer apparatus 22 together with the CCD camera 13.

The transfer apparatus 22 is framed on a platform 221 as shown in FIG. 2. A pair of support members 22a is mounted on the platform 221 at a determined distance. A X-direction supporter 22b extending in a determined direction (X-direction) is laid over the pair of support members 22a.

A Y-direction supporter 22c extending in a direction at a right angle to the X-direction supporter 22b, is mounted movable in the X-direction to the X-direction supporter 22b. The Y-direction supporter 22c itself is movable in the Y-direction on the X-direction supporter 22b.

In the example of FIG. 2, an end of the Y-direction supporter 22c is branched in a T-shape. To an end side of the T-shaped part is attached a first Z-direction supporter 22d, and to the other end side of the T-shaped part is attached a second Z-direction supporter 22e. The first and second Z-direction supporters 22d and 22e are movable in the direction at a right angle to both the X-direction supporter 22b and the Y-direction supporter 22c (the Z-direction).

The laser slit light emitting section 12 and CCD camera 13 are attached to the first Z-direction supporter 22d via a rotating body 22f, and the welding torch 21 is attached to the second Z-direction supporter 22e via a torch rotating member 22g and a torch weaving member 22h. Further, a mounting base 24 having a mounting stage 24a for placing the member to be repaired (blade) is mounted on the platform 221. A stage rotating body 24b and a stage inclining body 24c are provided to the mounting base 24, and the mounting stage 24a is driven in three axial directions by the stage rotating body 24b and stage inclining body 24c, as described later.

Next, the working of the automatic crack repairing apparatus composed as described above will be explained.

Figure 3:
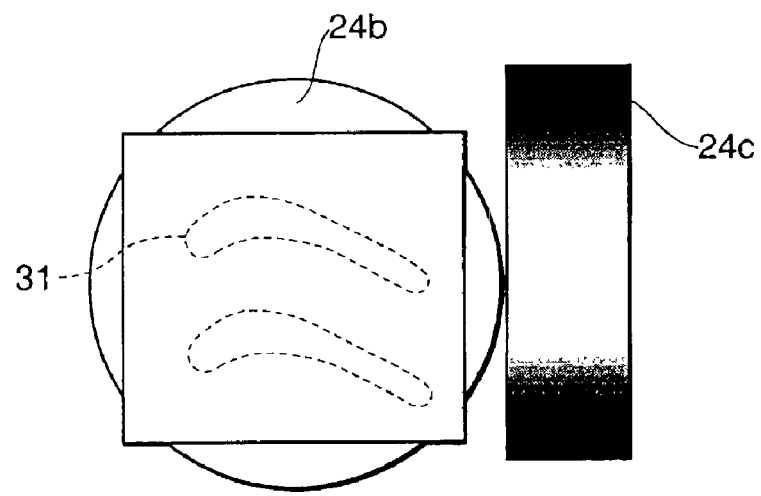
FIG. 3 is an illustration showing the relation of positions between a mounting stage rotating body and mounting stage inclining body.

First, the blade 31, the member to be repaired, is placed on the mounting stage 24a. The positional relation among the blade 31, the rotating body 24b, and inclining body 24c is as shown in FIG. 3. Then, the position, direction, width, and depth of the crack in the blade 31 are recognized. To be concrete, three-dimensional information of each of a plurality of members to be repaired is stored in the memory 18, and the total controller 17 reads the concerned three-dimensional information from the memory according to the blade selection command given from the input device 17a to recognize the three-dimensional image of the concerned blade from the memory 18.

The total controller 17 allows the remote camera 11 to take a picture of the whole of the blade 31 via the camera controller 14. The entire image of the blade 31 is sent to the image processing apparatus 16, which recognize the presence or absence of cracks and branch points, and their rough positions by shading. The rough position (three-dimension coordinates) of a crack is determined by interpolation based on the information of the entire image. That is, the crack information including the presence or absence of cracks and branch points and their rough positions (including direction) are obtained in the image processing apparatus 16 based on the picture taken by the remote camera 11. The crack information is given to the total control apparatus 17.

After the rough position of the crack is determined, the total controller 17 allows the Y-direction supporter 22c to be moved in the direction of X and Y by a servomotor (not shown in the drawing) via the servomotor controller 15 to position the first Z-direction supporter 22d above the mounting stage 24a (the position of the mounting stage 24a is predetermined).

Further, the total controller 17 allows the first Z-direction supporter 22d to be fine-adjusted in the three axis direction via the servomotor controller 15 based on the rough position of the crack, and the camera controller 14 allows the camera rotating body 22f to be rotated so that the laser slit light emitting section 12 and CCD camera 13 are positioned to the determined position in relation to the start point of the crack. That is, laser slit light emitting section 12 is positioned so that the laser slit light crosses the aperture of the crack and the CCD camera 13 is positioned so that it receives the laser slit light in the direction inclined by a determined angle from the laser slit light.

Then, the total controller 17 allows the laser slit light to be emitted from the laser slit light emitting section 12 via the camera controller 14, and the laser slit light is received by CCD camera 13. The received light is given from the CCD camera 13 to the image processing apparatus 16 via the camera controller 14 as a crack image. As the image taken by the CCD camera 13 is an image taken by the light section method, the depth of the crack can be recognized from the image of the crack in the image processing apparatus 16. Thus, the width, depth, and position (coordinates) of the start point of the crack (hereafter referred to as the start point data of the crack) is determined from the image taken by the CCD camera 13 in the image processing apparatus 16.

Then, the total controller 17 controls the first Z-direction supporter 22d and camera rotating body 22f to move the laser slit light emitting section 12 and CCD camera 13 by the predetermined distance (spacing) according to the information of the rough position of the crack (this new position is called the first midpoint). The picture of the crack is taken at the first midpoint by the light section method to determine the width, depth, and position (coordinates) of the crack at the first midpoint (hereafter referred to as the first midpoint data of the crack).

Thus, the width, depth, and position (coordinates) of the crack are determined successively by moving the laser slit light emitting section 12 and CCD camera 13 and taking the picture of the crack by the light section method, by the predetermined distance according to the information of the rough position of the crack. When the laser slit light emitting section 12 and CCD camera 13 are moved to the $n^{th}$ midpoint, the width, depth, and the position (coordinates) at the $n^{th}$ midpoint on the crack are determined (n is an integer between 1 and N, where N is an integer equal to or larger than 1). The determination of a crack is finished when the width, depth, and coordinates of the end point of the crack are determined (hereafter referred to as the end point data of the crack).

Figure 4:
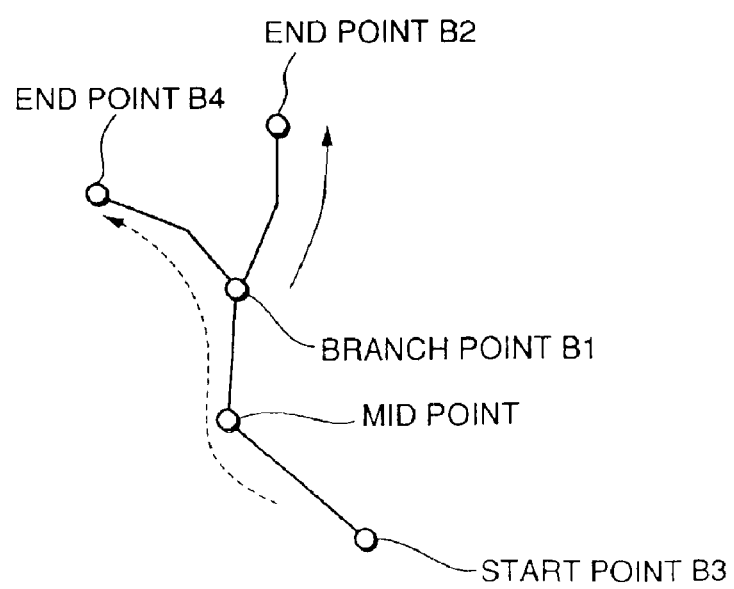
FIG. 4 is an illustration showing the position the picture of a crack is taken.
Figure 5A:
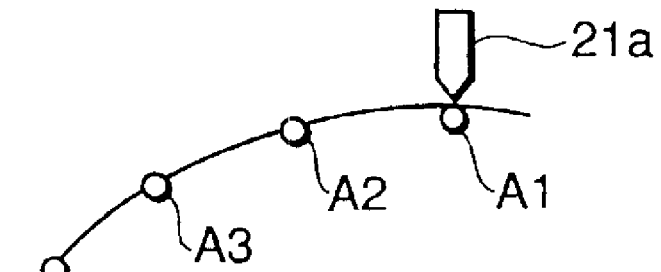
FIG. 5(A) is an illustration showing the welding of the start point of the crack.
Figure 5B:
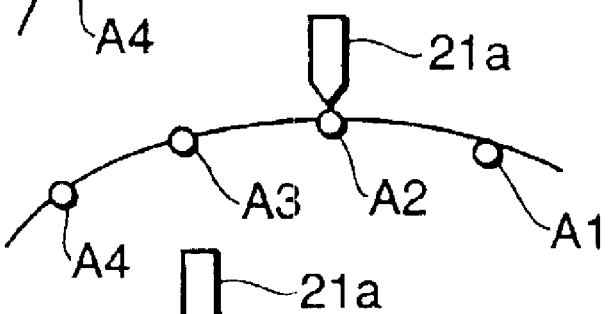
FIG. 5(B) is an illustration showing the welding of a first midpoint of the crack.
Figure 5C:
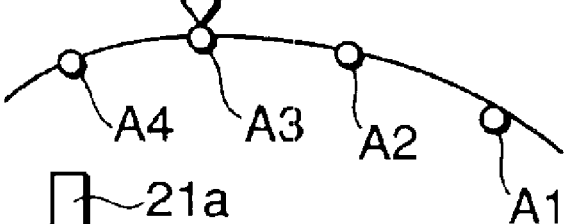
FIG. 5(C) is an illustration showing the welding of a second midpoint of the crack.
Figure 5D:
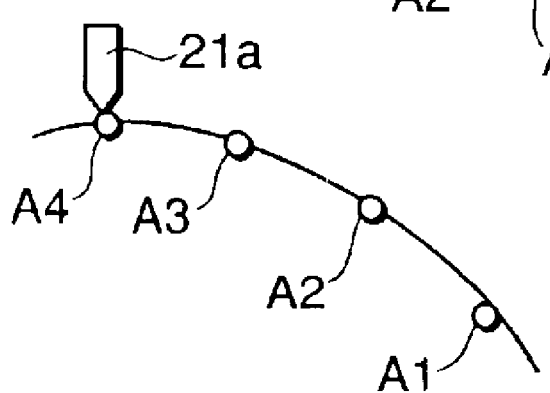
FIG. 5(D) is an illustration showing the welding of an endpoint of the crack.
Figure 6:
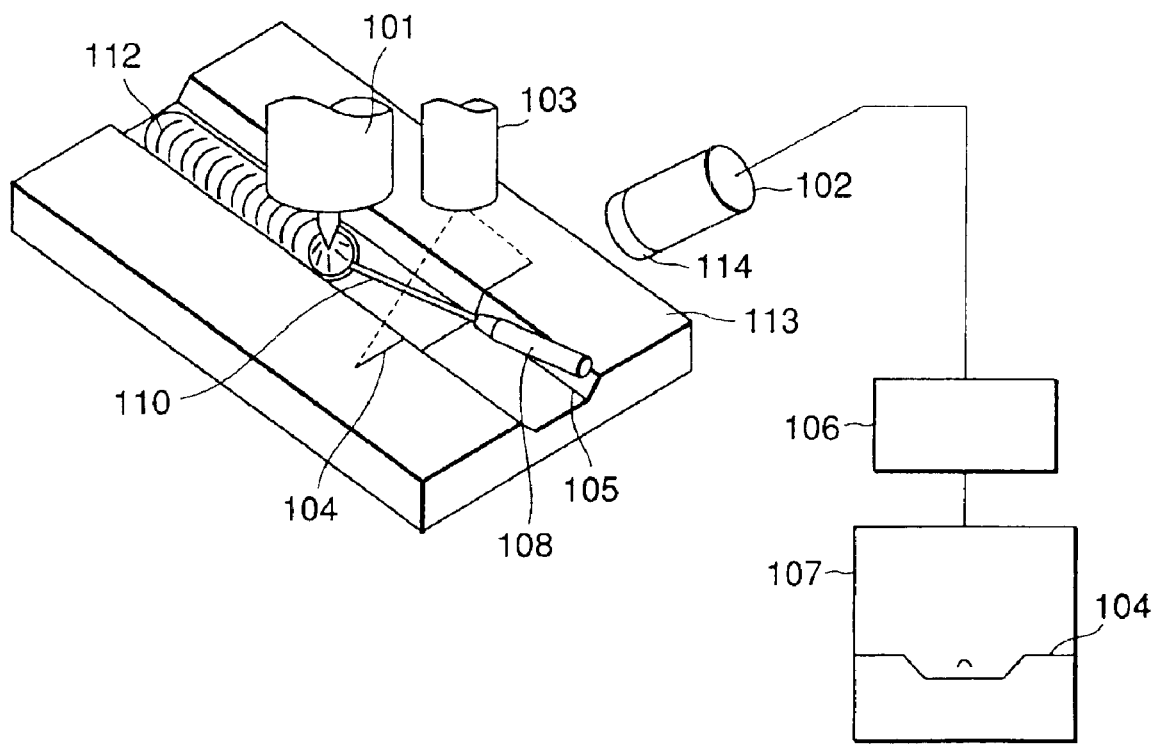
FIG. 6 is a schematic representation of a light section method in the field of welding.
Figure 7A:
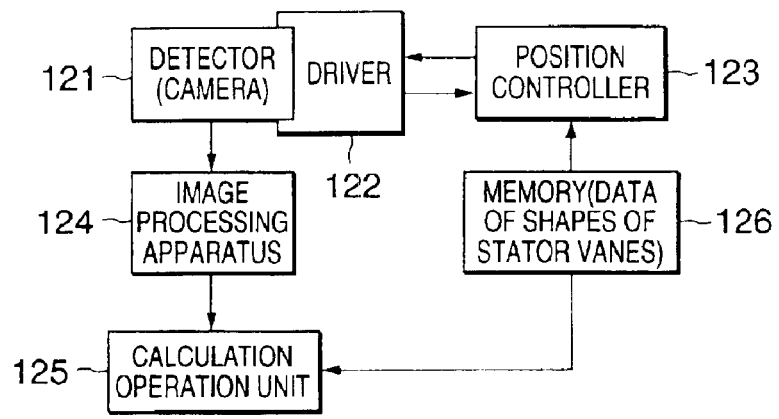
FIG. 7(A) is a block diagram of a crack repairing apparatus of the prior art.
Figure 7B:
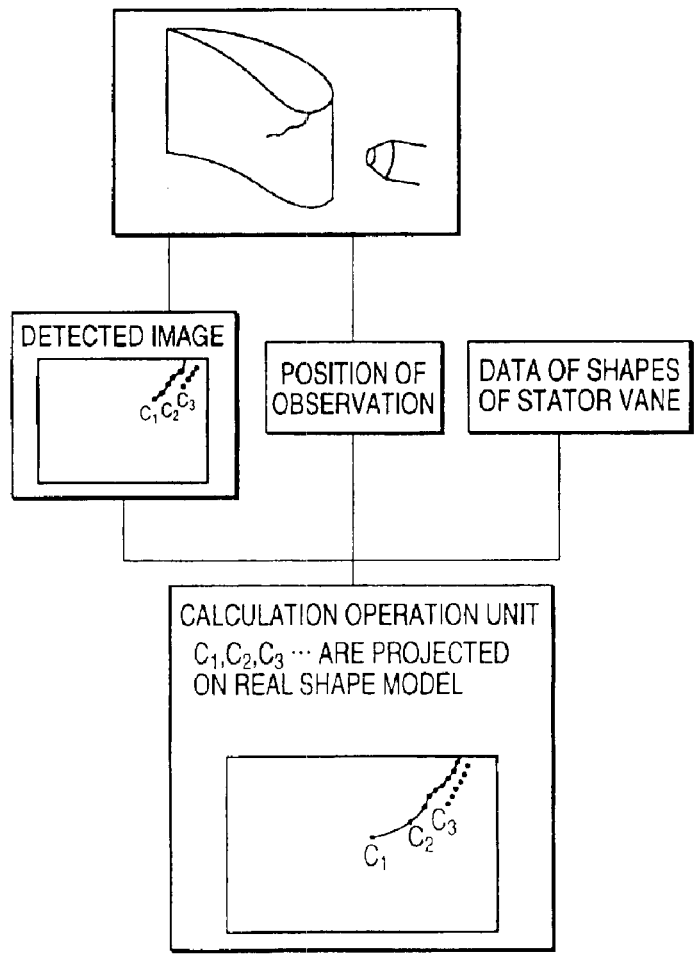
FIG. 7(B) is a block diagram showing the procedure of determining real length from the length of the projected image.

When the crack has a branch point B1 as shown in FIG. 4, the determination of the crack is again carried out starting from the branch point B1 to the end point B2 of the branch (this is shown by the solid arrow line in the drawing), which is recognized as a crack.

On the other hand, the picture of the other branch of the crack is taken starting from the start point B3 to the end point B4 of the branch to be recognized as another crack (this is shown by the broken arrow line in the drawing).

The information of the cracks at the start points, at $n^{th}$ midpoint, and at the end points are given to the total controller 17, which allows the memory 18 to store the information at each point as crack data at the series of points.

After crack data at the series of points for all cracks in the blade 31 are determined, grinding is carried out for each crack. The grinding is performed based on the crack data at the series of points stored in the memory 18. The direction of the straight-line segment connecting adjacent points is determined in the total controller 17. The grinding controller 20 is controlled to allow, for example, a pencil type grinding head (not shown in the drawing) to grind the cracks along the crack data at the series of points according to the predetermined grinding procedure. The grinding head is attached, for example, to the second Z-direction supporter 22e, which is controlled to move the grinding head according to the crack data at the series of points in order to grind the cracks.

After the grinding of the cracks is over, then the welding of the cracks is carried out. The grinding is done for every point of the series of points in the way the grinding head is directed at right angles with each straight-line segment.

When welding, the welding torch 21 and wire supplier 23 are controlled also according to the crack data at the series of points.

It is supposed in FIG. 5 that crack data at the series of points is composed of a start point, a first midpoint, a second midpoint, and an end point. First, the head (torch head) 21a of the welding torch 21 is directed at a right angle to the straight-line segment at the start point and welding is done for the start point as shown in FIG. 5(A). Welding is done similarly for the first midpoint A2, second midpoint A3, and end point A4 as shown in FIG. 5(B)~FIG. 5(D) respectively according to the crack data at the series of points. So-called multi-layer welding is done depending on the width and depth of the crack. That is to say, welding is done according to each determined depth, and multi-layer welding is done at a point at which the crack is deep.

In the above description, the remote camera 11 is used to take the picture of the whole surface of the blade 31, however, one camera may be used to take the picture of the whole surface of the blade 31 and to take pictures by the light section method. In this case, a camera having a zoom lens, etc. is used, and picture taking can be done with wide and narrow fields of view. Photographing by the light section method is done with a narrow field of view.

So-called shade photographing may be used instead of the light section method. In this case, a height sensor or the like is used, for the depth of crack can not be determined even though the position and width of the crack can be determined, by the shade photographing.

When photographing the crack in a narrow field view, the spacing between each point from the start point through $n^{th}$ midpoint to end point is determined so that it can be assumed as a straight line. By determining the spacing like this, the welding along the crack can be carried out easily.

As has been described in the forgoing, according to the present invention, when repairing the cracks produced in a member to be repaired such as a blade, the position of the cracks is obtained as rough position information from the picture of the whole surface of the member to be repaired taken in a wide field view. Then the crack is photographed in a narrow field view at the predetermined spacing along the crack based on the rough position information, to obtain the position, width, and depth of the crack at each predetermined spacing, which composes crack data at the series of points. The crack is repaired based on the crack data at the series of points.

Therefore, the invention brings about the effect that the cracks produced in the member to be repaired can be automatically repaired with good accuracy.

What is claimed is:

1. An automatic repairing apparatus used in repairing cracks produced in a member to be repaired, comprising:
   a first photographing means for taking a picture of the member to be repaired in a wide field view in order to obtain a wide field image, thereof;
   an image processing means for obtaining rough position information of the cracks, including information of the presence and absence of cracks and the positions thereof in the member to be repaired, by processing the wide field image; and
   a second photographing means for obtaining a narrow field image of the cracks by photographing the cracks in a narrow field view at each point at a spacing predetermined based on the rough position information; and
   wherein said image processing means processes the narrow field image to obtain the crack data at a series of points, including information of the position, width, and depth of the cracks at each point spaced by a predetermined distance, by processing the narrow field image.

2. The automatic repairing apparatus according to claim 1, and further comprising a repairing means for repairing the cracks based on the crack data at the series of points.

3. The automatic repairing apparatus according to claim 1, wherein said second photographing means photographs the cracks according to a light section method.

4. A method of automatically repairing cracks, comprising:
   obtaining rough position information of cracks, including information relating to the presence and absence of cracks and the positions thereof, by processing a wide field image obtained by taking a picture of a member to be repaired with a wide field view;
   obtaining crack data at a series of points along the cracks, including information of the position, width, and depth of the cracks at each point at a predetermined spacing along the cracks, by processing a narrow field image of the cracks obtained by photographing the cracks at each point at the predetermined spacing based on the rough position information; and
   repairing the cracks in accordance with the crack data at the series of points;
   wherein said repairing comprises grinding the cracks based on the crack data at the series of points and welding the cracks based on the crack data at the series of points.

5. The method of claim 4, wherein said obtaining crack data at the series of points comprises using a light section method to obtain the crack data.

6. The method of claim 4, wherein the predetermined spacing is a distance between adjacent points at which one of the cracks is photographed in said obtaining crack data at the series of points, and the distance is determined in a range in which a line segment connecting the adjacent points can be assumed to be a straight-line segment.

7. A method of automatically repairing cracks, comprising:
   obtaining rough position information of cracks, including information relating to the presence and absence of cracks and the positions thereof, by processing a wide field image obtained by taking a picture of a member to be repaired with a wide field view;
   obtaining crack data at a series of points along the cracks, including information of the position, width, and depth of the cracks at each point at a predetermined spacing along the cracks, by processing a narrow field image of the cracks obtained by photographing the cracks at each point at the predetermined spacing based on the rough position information;
   wherein the predetermined spacing is a distance between adjacent points at which one of the cracks is photographed in said obtaining crack data at the series of points, and the distance is determined in a range in which a line segment connecting the adjacent points can be assumed to be a straight-line segment.

8. The method of claim 7, wherein said obtaining crack data at the series of points comprises using a light section method to obtain the crack data.

* * * * *